United States Patent [19]

Hodges et al.

[11] Patent Number: 5,041,552

[45] Date of Patent: Aug. 20, 1991

[54] AMINO ACID DERIVATIVES WITH ANGIOTENSION II ANTAGONIST PORPERTIES

[75] Inventors: John C. Hodges; Ila Sircar, both of Ann Arbor, Mich.

[73] Assignee: Warner-Lambert Company, Morris Plains, N.J.

[21] Appl. No.: 529,071

[22] Filed: May 25, 1990

[51] Int. Cl.⁵ .............................................. C07D 249/08
[52] U.S. Cl. ............................. 548/263.8; 548/264.2; 548/266.8; 548/267.8
[58] Field of Search ............... 548/264.2, 267.8, 263.8, 548/267.8, 266.8

*Primary Examiner*—Mary C. Lee
*Assistant Examiner*—Peter Davis
*Attorney, Agent, or Firm*—Elizabeth M. Anderson

[57] ABSTRACT

This invention relates to novel amino acid derivatives which antagonize the binding of angiotensin II to its receptors. The compounds are useful in the treatment of hypertension, heart failure, glaucoma, and hyperaldosteronism. Methods of making the compounds, novel intermediates useful in the separation of the compounds, compositions containing the compounds and methods of using them are also covered.

4 Claims, No Drawings

AMINO ACID DERIVATIVES WITH ANGIOTENSION II ANTAGONIST PORPERTIES

BACKGROUND OF THE INVENTION

The instant invention relates to novel amide and urea derivatives of α-aminoacids containing substituted imidazole or 1,2,4-triazole moieties which antagonize the binding of angiotensin II (AII) to cellular receptors. This AII antagonist property renders these compounds useful for treatment of angiotensin-related hypertension.

The enzyme renin acts on a blood plasma $\alpha_2$-globulin, angiotensinogen, to produce angiotensin I, which is then converted by angiotensin-converting enzyme to AII. The latter substance is a powerful vasopressor agent which has been implicated as a causative agent for producing high blood pressure in various mammals, such as rats, dogs, and humans. The compounds of this invention inhibit the action of AII at its receptors on target cells and thus prevent the increase in blood pressure produced by this hormone-receptor interaction. By administering a compound of the instant invention to a species of mammal with hypertension due to AII, the blood pressure is reduced. The compounds of the invention are also useful for the treatment of congestive heart failure, hyperaldosteronism and glaucoma.

European Application Number 253,310 discloses imidazoles of the formula

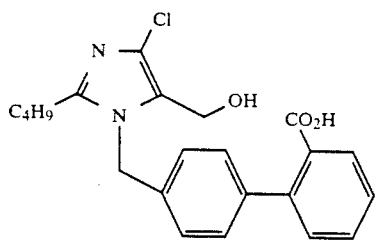

The compounds are disclosed as having utility in treating hypertension and congestive heart failure.

European Application Number 323,841 discloses substituted pyrrole-, pyrazole-, and triazole-containing compounds of the formulas

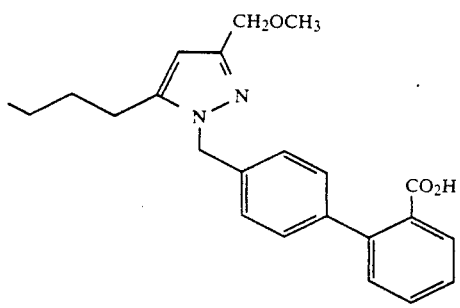

and

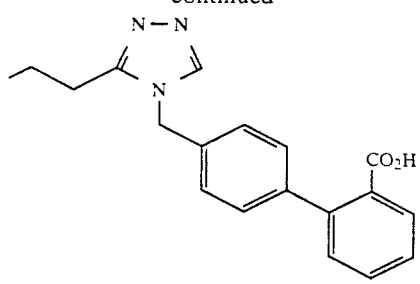

European Application Number 324,377 discloses a pharmaceutical composition of a diuretic or a nonsteroidal antiinflammatory drug useful for blocking the angiotensin II receptor.

U.S. Pat. No. 4,355,040 discloses imidazole-5-acetic acid derivatives of the formula

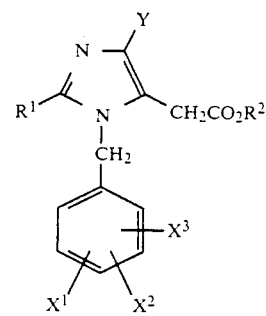

wherein $R^1$ is lower alkyl, cycloalkyl or, phenyl which may be substituted with one to three of halogen, nitro, amino, mono(lower alkyl)amino, di(lower alkyl)amino, lower alkyl, lower alkoxyl, benzyloxyl or/and hydroxyl; $X^1$, $X^2$ and $X^3$ are each hydrogen, halogen, nitro, amino, lower alkyl, lower alkoxyl, benzyloxyl or hydroxyl; Y is halogen and $R^2$ is hydrogen or lower alkyl; provided that $X^1$ is halogen, lower alkyl, lower alkoxyl, benzyloxyl or hydroxyl when $R^1$ is unsubstituted or substituted phenyl only with one halogen, di(lower alkyl)amino, lower alyl or lower alkoxyl, and its salts. The compounds are disclosed as having hypertensive activity.

SUMMARY OF THE INVENTION

The instant invention concerns novel amino acid derivatives which antagonize the binding of angiotensin II to its receptors. The compounds are those of formula

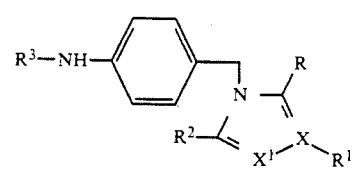

and the pharmaceutically acceptable acid addition or basic salts thereof wherein X, $X^1$, R, $R^1$, $R^2$, and $R^3$ are as defined below.

The invention also includes a pharmaceutical composition comprising an antihypertensive effective amount of a compound of Formula I above in admixture with a pharmaceutically acceptable carrier or excipient and a method for treating renin-associated hypertension in a mammal suffering therefrom which comprises administering to said mammal the above pharamceutical composition in unit dosage form.

Further the invention includes a pharmaceutical composition comprising an amount of a compound of Formula I above effective for treating renin-associated hyperaldeosteronism in admixture with a pharmaceutically acceptable carrier or excipient, and a method for treating hyperaldosteronism in a mammal suffering therefrom comprising administering to said patient the above pharmaceutical composition in unit dosage form.

Also the invention includes a pharmaceutical composition comprising an amount effective for treating congestive heart failure of a compound of Formula I above in admixture with a pharmaceutically acceptable carrier or excipient and a method of treating congestive heart failure in a patient suffering therefrom comprising administering to said patient the above pharmaceutical composition in unit dosage form.

Also the invention includes a pharmaceutical composition comprising an amount of a compound of Formula I above effective for treating glaucoma in admixture with a pharmaceutically acceptable carrier or excipient; and a method of treating glaucoma in a patient suffering therefrom comprising administering to said patient the above pharmaceutical composition in unit dosage form.

The instant invention further includes methods for making compounds of Formula I and novel intermediates useful in the preparations.

DETAILED DESCRIPTION

The following table provides a dictionary of the terms used in the description of the invention. The natural L-amino acids are designated by the standard three letters (see Lubert Stryer, *Biochemistry*, W. H. Freeman and Co., 1975, page 17).

TABLE I

| Abbreviation | |
|---|---|
| | Amino Acid |
| NIA | L-3-Cyanoalanine |
| AMA | Aminomalonic acid |
| (tBuO)AMA | DL-Aminomalonic acid, mono-t-butyl ester |
| (EtO)AMA | DL-Aminomalonic acid, monoethyl ester |
| PHG | L-Phenylglycine |
| CHA | L-Cyclohexylalanine |
| | Protecting Group |
| BOC | Tert-Butyloxycarbonyl |
| CBZ | Benzyloxycarbonyl |
| Bn | Benzyl |
| Ac | Acetyl |
| | Solvents |
| MeOH | Methanol |
| DMF | N,N-Dimethyl formamide |
| THF | Tetrahydrofuran |
| EtOAc | Ethyl acetate |
| | Reagents |
| DCC | N,N'-Dicyclohexyl carbodiimide |
| HOBT | 1-Hydroxybenzotriazole |
| TFA | Trifluoroacetic acid |

The compounds of the present invention are represented by formula

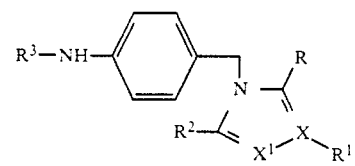

and the pharmaceutically acceptable acid addition of base salts thereof, wherein:

X and Xhu 1 are each independently carbon or nitrogen;

R and $R^1$ are each independently
hydrogen,
halogen,
lower alkyl,
alkyl carboxylate,
trihalomethyl,
acetyl ester,
cyano,
cyanomethyl,
acetamide,
alkoxymethyl,
hydroxymethyl,
alkylthiomethyl,
thiomethyl,
COOH,
CHO,
1-oxoalkyl,
2-oxoalkyl, or
3-oxoalkyl
with teh proviso that when X is nitrogen, $R^1$ is absent, $R^2$ is propyl,
butyl,
—$CH_2CH=CH_2$,
—$CH=CHCH_3$,
—$CH_2CH=CH—CH_3$,
—$CH=CHCH_2Ch_3$,
—$CH_2CH_2CH=CH_2$
—$CH_2C\equiv CH$,
—$C\equiv C—CH_3$,
—$C\equiv C—CH_d$,
—$CH_2C\equiv CCH_3$,
—$CH_2CH_2C\equiv CH$,
—$SCH_3$,
—$SC_2H_5$,
—$SC_3H_7$,
—$SC_4H_9$,
—$OCH_3$,
—$OC_2H_5$,
—$OC_3H_7$,
—$OC_{4l}H_9$
—$SCH_2CH=CH_2$
—$OCH_2CH=CH_2$,
—$SCH_2C\equiv CH$, or
—$OCH_2C\equiv CH$;
and
$R_3$ is

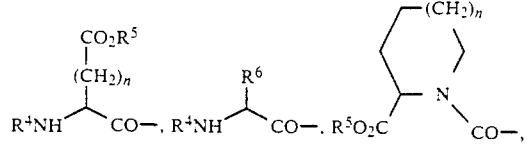

-continued
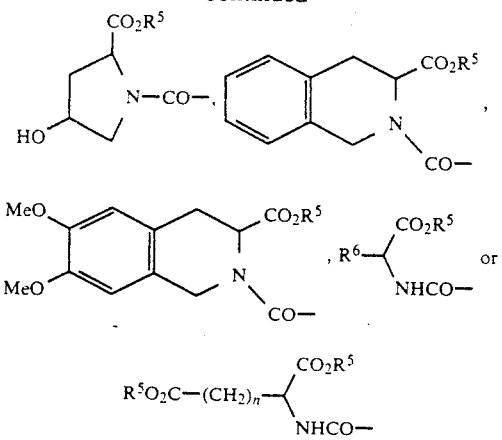
wherein
R₄ is
  CBZ,
  BOC,
  -COPh,
  —COCH₂CH₃,
  —COCH₃,
  —COCF₃,
  —CONH₂,
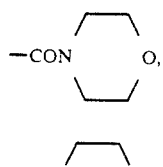
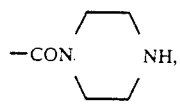
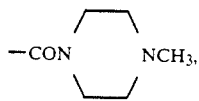
—CONHCH₃,
—CON(CH₃)₂,
—SO₂CH₃,
—SO₂CF₃,
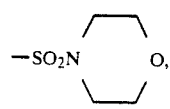
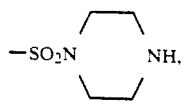
-continued
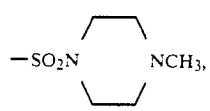
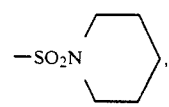
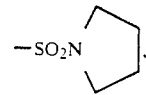
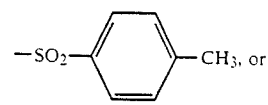
—SO₂Ph;
R₅ is
  H,
  CH₃,
  C₂H₅,
  t—C₄H₉,
  CH₂Ph;
n is 0-3; and
R₆ is
  H
  CH₃,
  C₂H₅,
  C₃H₇
  i—C₃H₇,
  C₄H₉,
  i—C₄H₉,
  CH₂CH(CH₃)CH₂CH₃,
  CH₂CH=CH₂,
  CH₂-cyclohexyl,
  CH₂—Ph,
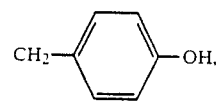
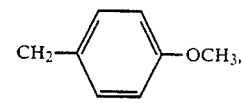
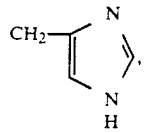
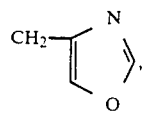
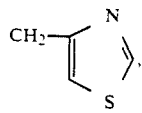

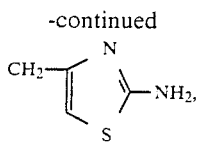

CH₂CN,
(CH₂)₃NH₂,
(CH₂)₂,

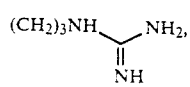

CH₂OH
CH(CH₃)OH,
CH₂SH,
CH₂CH₂SCH₃,

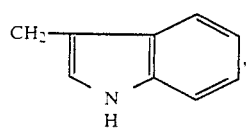

CH₂CONH₂, or
CH₂CH₂CONH₂.

Preferred compounds of the instant invention are those of FOrmula I wherein
X and X¹ are each independently carbon or nitrogen;
R and R¹ are each independently,
—CH₂OH,
—CH₂SH
—CH₂OCH₃,
—CH₂SCH₃,
—CHO
—CO₂CH₃
—C≡N

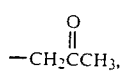

—CO₂C₂H₅;
—COOH,
—CF₃,
—CH₃,
—H,
—Cl,
—Br,
—F,
—CH₂CO₂CH₃,
—CH₂CO₂C₂H₅,
—CH₂≡N,
—CH₂CONH₂,
—CH₂CONHCH₃, or
—CH₂CON(CH₃)₂
with the proviso that when X is nitrogen, R¹ is absent;
R²
is propyl,
butyl,
thiomethyl,
thioethyl,
thiopropyl,
thiobutyl,
—CH₂CH=CH₂,
—CH₂CH=CH—CH₃,
—CH₂CH₂CH=CH₂,
—CH₂C≡CCH₃,
—CH₂CH₂C≡CH,
—OCH₃,
—OCH₂H₅,
—OC₃H₇,
—OC₄H₉,
—SCH₂CH=CH₂ or
—OCH₂CH=CH₂; and
R₃ is as above.

More preferred compounds of the instant invention are those compounds of Formula I wherein
X is carbon or nitrogen;
X¹ is nitrogen;
R and R¹ are each independently,
—H,
—CH₂OH,
—CH₂OCH₃,
—CH₂CO₂CH₃,
—Cl
—Br, or
—CF₃
with the proviso that when X is nitrogen R¹ is absent;
R₂ is
—C₄H₉,
—C₃H₇,
—SC₂H₅, or
—SC₃H₇; and
R₃ is

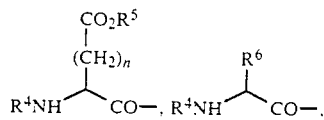

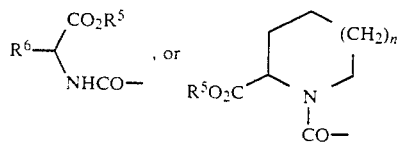

wherein
R⁴ is
CBZ,
BOC,
COPh,
COCH₃,

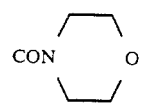

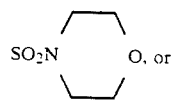

SO₂Ph;
n is 0-2;
R⁵ is
—H,
—CH₃,
—CH₂H₅,

—t—$C_4H_9$ or
—$CH_2Ph$; and $R^6$ is
—$CH_3$,
—$iC_3H_7$,
—$iC_4H_9$,
—$CH_2CH(CH_3)CH_2CH_3$,
—$CH_2pH$,

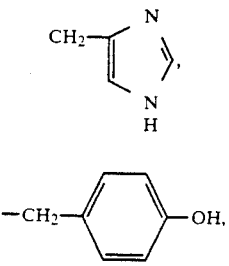

—$CH_2OH$,
—$CH_2SH$, or
—$CH(CH_3)OH$.

Most especially preferred compounds of the instant invention are selected from the list consisting of:

(S)[2-[[4-[[2-Butyl-4-chloro-5-(hydroxymethyl)-1-H-imidazol-1-yl]methyl]phenyl]amino]-1-(cyanomethyl)-2-oxoethyl]-carbamic acid, phenylmethyl ester;

(S)[2-[[4-[[2-Butyl-4-chloro-5-(hydroxymethyl)-1-H-imidazol-1-yl]methyl]phenyl]amino]-1-]]4-hydroxyphenyl)methyl]-2-oxoethyl]-carbamic acid, 1,1-dimethylethyl ester;

(S)-[2-[[4-[[2-Butyl-5-(hydroxymethyl)-1H-imidazol-1-yl]methyl]phenylamino-l-[(4-hydroxy-phenyl)methyl-2-oxoethyl]-carbamic acid, 1,1-dimethylethyl ester;

(S)-4-[[4-[3-(Ethylthio)-5-(hydroxymethyl)-4H-1,2,4-triazol-4-yl]methyl]phenyl]amino]-4-oxo-3-[(phenylmethoxy)carbonyl]amino]-butanoic acid;

(S)-4-[[4-[[2-Butyl-4-chloro-5-(hydroxymethyl)-1H-imidazol-1-yl]methylphenyl]amino]-4-oxo-3-[[(phenylmethoxy)carbonyl]aminobutanoic acid;

(S)-4-[[4-[[2-Butyl-4-chloro-5-(hydroxymethyl)-1H-imidazol-1-yl]methyl]phenyl]amino]-4-oxo-3[[(phenylmethoxy)carbonyl]amino]butanoic acid, 1,1-dimethylethyl ester;

(S)-4-[[4-[[3-(Ethylthio)-5-(hydroxymethyl)-4H-1,2,4-triazol-4-yl]methylphenyl]amino]-4-oxo-3-[[phenylmethoxy)carbonyl]amino]-butanoic acid;

(RS)-3-[[4-[[2-Butyl-4-chloro-5-(hydroxymethyl)-1H-imidazol-1-yl]methyl]phenyl]amino]-2-[[(1,1-dimethylethoxy)carbonyl]amino]-3-oxo-propanoic acid, ethyl ester;

(RS)-3-[[4-[[2-Butyl-4-chloro-5-(hydroxymethyl)-1H-imidazol-1-ylmethylphenyl]amino]-2-[[(l,ldimethylethoxy)carbonyl]amino]-3-oxo-propanoic acid;

(RS)-3-[[4-[[2-Butyl-4-chloro-5-(hydroxymethyl)-1H-imidazol-1-yl]methyl]phenyl]amino-3-oxo-2-[[phenylmethoxy)carbonylamino]-propanoic acid, ethyl ester;

(RS)-3-[[4-[[2-Butyl-4-chloro-5-(hydroxymethyl)-1H-imidazol-1-yl]methylphenyl]amino]-3-oxo-2[[(phenylmethoxy)carbonyl]amino]-propanoic acid;

(RS)-2-(Acetylamino)-3-[[4-[[2-butyl-4-chloro-5-(hydroxymethyl)-1H-imidazol-1-yl]methyl]phenyl]amino]-3-oxo-propanoic acid 1,1-dimethylethyl ester;

(S)-N-4-[[2-Butyl-4-chloro-5-(hydroxymethyl)-1H-imidazol-1-yl]methylphenyl-2-[(4-morpholinylsulfonyl)amino]-3-phenylpropanamide;

(S)-2-(Benzenesulfonylamino)-N-[4-[[2-butyl-4-chloro-5-(hydroxymethyl)-1H-imidazol-1-ylmethyl]phenyl]-3-phenylpropanamide; and 1-[[[4-[[2-Butyl-4-chloro-5-(hydroxymethyl)-1H-imidazol-1-yl]methylphenyl]amino]carbonyl]-2-pyrrolidinecarboxylic acid, methyl ester.

The compounds of the instant invention include solvates, hydrates, and pharmaceutically acceptable acid addition salts of the basic compounds of Formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base.

The compounds of the present invention possess one or more chiral centers and each center may exist in the R(D) or S(L) configuration. The present invention includes all enantiomeric and epimeric forms as well as the appropriate mixtures thereof.

The instant invention includes a process for the preparation of triazolo-containing compounds of Formula I which comprises:

(a) reacting 4-nitrobenzylamine with di-2-pyridylthiocarbonate to produce the corresponding isothiocyanate, (b) adding an acid hydrazide to the isothiocyanate to produce the corresponding thiosemicarbazide, (c) cyclizing using an aqueous inorganic base and heat and then acidification to produce the corresponding triazole-thione, (d) alkylating the product of Step (c) with an alkylhalide in the presence of an organic base in a polar solvent and subsequent hydrogenation to produce an aminobenzyltriazole, (e) acylating with a desired protected amino acid and subsequent deprotecting of the amino acid to produce a compound of Formula I, which may be converted if desired to a pharmaceutically acceptable salt thereof.

The instant invention also includes a process for the preparation of imidazole-containing compounds of Formula I which comprises:

(a) reducing and acylating

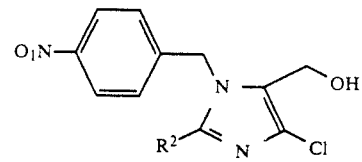

wherein $R^2$ is as defined above with a desired amino acid derivative and (b) deprotecting the product of Step (a) to produce a desired compound of Formula I which may, if desired, be converted to a corresponding pharmaceutically acceptable salt thereof.

Novel compounds useful in the synthesis of compounds of the instant invention are:

[4-(Nitrophenyl)methyl-carbamothioic acid, (hydroxyacetyl)hydrazide;

5-Mercapto-4-[(4-nitrophenylmethyl]-4H-1,2,4-triazol-3-methanol;

5-(Ethylthio)-l-(4-nitrophenyl)methyl]-1H-1,3,4-triazole-2-methanol;

1-[(4-Aminophenyl)methyl-5-(ethylthio)-1H-1,3,4-triazole-2-methanol

1-[(4-Nitrophenyl)methyl-5-(1-propylthio)-4-triazole-2-methanol; and

1-[(4-Aminophenyl)methyl-5-(1-propylthio)-1H-1,3,4-triazole-2-methanol.

The term protecting group refers to those groups intended to protect against undesirable reactions during synthetic procedures includes but is not limited to BOC, CBZ, Bn, and Ac.

The term lower alkyl refers to straight or branched chain alkyl radicals containing from one to six carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methyl-pentyl, 2,2-dimethylpropyl, n-hexyl, and the like.

The term halogen refers to bromine, chlorine, and fluorine.

The term alkyl carboxylate refers to groups —$CO_2$alkyl wherein alkyl is as above; the preferred alkyls are methyl and ethyl.

The term trihalomethyl refers to the halogens as above; the preferred group is trifluoromethyl.

The term acetyl ester refers to groups —$CH_2CO_2$alkyl wherein alkyl is as described above; the preferred groups are $CH_2CO_2CH_3$ and $CH_2CO_2C_2H_5$.

The term acetamide refers to groups —$CH_2CON(R)_2$ wherein the R substituents can each independently be hydrogen or lower alkyl; the preferred acetamides are —$CH_2CONH_2$, —$CH_2CONHCH_3$, and —$CH_2CON(CH_3)_2$.

The term alkoxymethyl refers to groups —$CH_2CON(R)_2$ wherein the R substituent is lower alkyl as above; the preferred groups are —$CH_2OCH_3$ and —$CH_2OC_2H_5$.

The term alkylthiomethyl refers to groups wherein alkyl is as defined above; the preferred group is —$CH_2SCH_3$.

The terms 1-oxoalkyl, 2-oxoalkyl, and 3-oxoalkyl refer to groups wherein alkyl is as defined above;

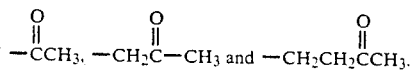

The syntheses of compounds of the Formula I are exemplified in Schemes I and II below. The first route begins with 4-nitrobenzylamine (2) which is converted in situ to its isothiocyanate by reacting with thiophosgene and an organic base such as triethylamine or by reacting with a thiophosgene equivalent such as di-2-pyridyl-thiocarbonate or thiocarbonyldiimidazole in an inert solvent such as dichloromethane, ether, tetrahydrofuran, or chloroform. Subsequent addition of an acid hydrazide such as glyoxylic acid hydrazide affords the thiosemicarbazide, 3. Cyclization occurs upon brief heating with an aqueous inorganic base such as KOH, NaOH, $K_2CO_3$, or $Na_2CO_3$. Acidification on work-up affords the triazole-thione, 4.

Alkylation at sulfur occurs by treatment with an alkyl halide such as ethyl iodide, propyl iodide, allyl bromide, or 1-bromo-2-butene in the presence of an organic base such as diisopropylethyl-amine or triethylamine in a polar solvent such as DMF or DMA. Subsequent hydrogenation over Raney nickel catalyst affords the aminobenzyl-triazole, 5. Acylation with a protected amino acid and subsequent deprotection affords Compounds 6- and -7 which are examples of compounds of the Formula I.

Strategies for carboxy activation of N-protected amino acids are well known to those skilled in the art of peptide synthesis. In the above synthesis numerous reagents of carboxy activation are useful including, but not limited to, DCC/HOBT, ethyl chloroformate/ triethylamine, BOP-Cl/triethylamine, and carbonyl diimidazole. Methods for activation of the amino acid carboxy terminus are discussed in "The Peptides. Analysis, Synthesis, Biology," E. Gross and J. Meienhofer, Eds., Academic Press, New York, N.Y., 1979.

An alternative method for connecting an amino acid to Fragment 5 involves the reaction of an isocyanate or carbamyl chloride derivative of an amino acid with 5 in a solvent such as THF, acetonitrile, DMF, methanol, or chloroform. Subsequent deprotection of the carboxy terminus gives 8 which is an example of a compound of Formula I with a urea linkage.

Scheme II shows a second route that employs 9, which is prepared in a manner analogous to that of Furakawa, et al, U.S. Pat. No. 4,355,040, Example 17, as the starting material. Similar to Scheme I, Compound 9 may be reduced and acylated by carboxyl-activated amino acid derivatives or by isocyanate derivatives of amino acids. Subsequent deprotection and/or exchange of N-Acyl groups using methods standard to the art of amino acid chemistry afford compounds such as 11, 12, and 13 which are examples of a compound of Formula I.

Scheme I

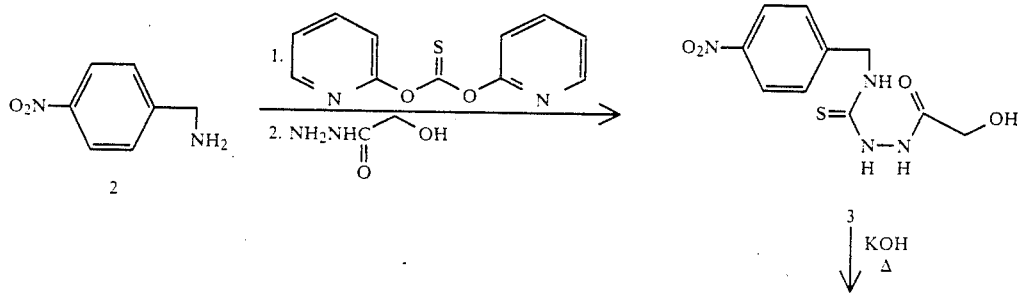

-continued
Scheme I
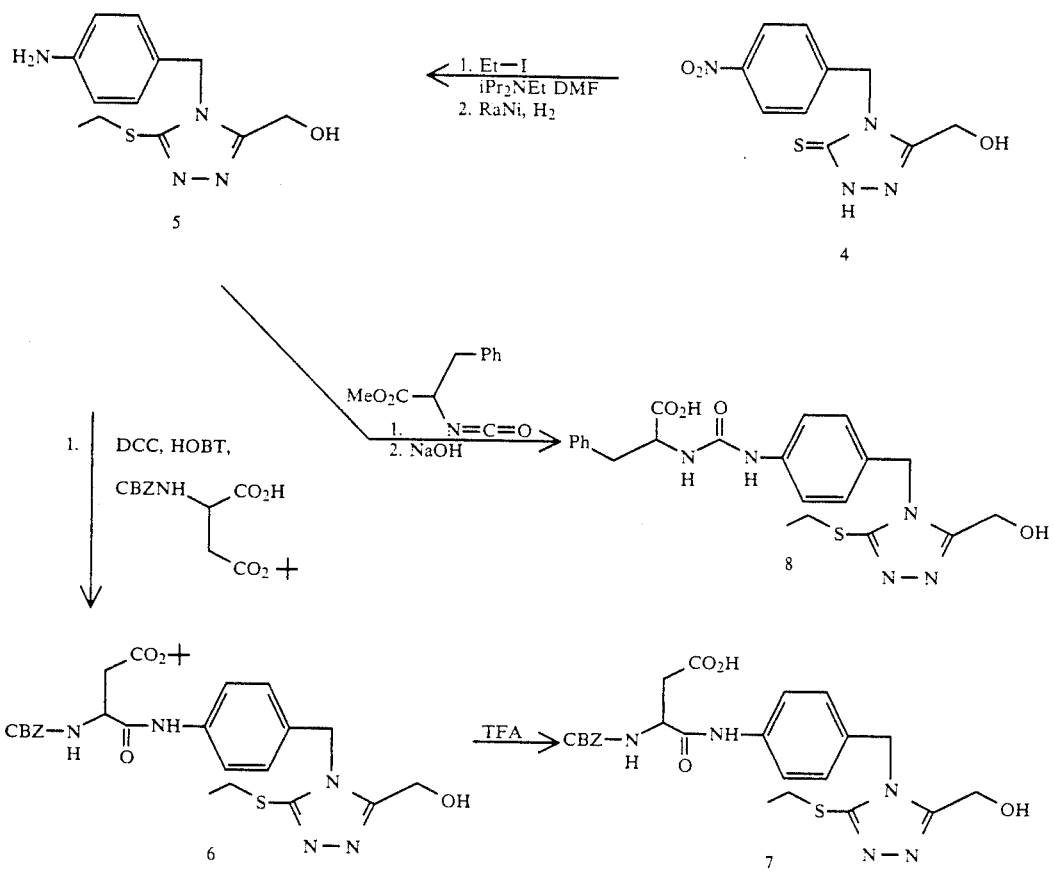
Scheme II
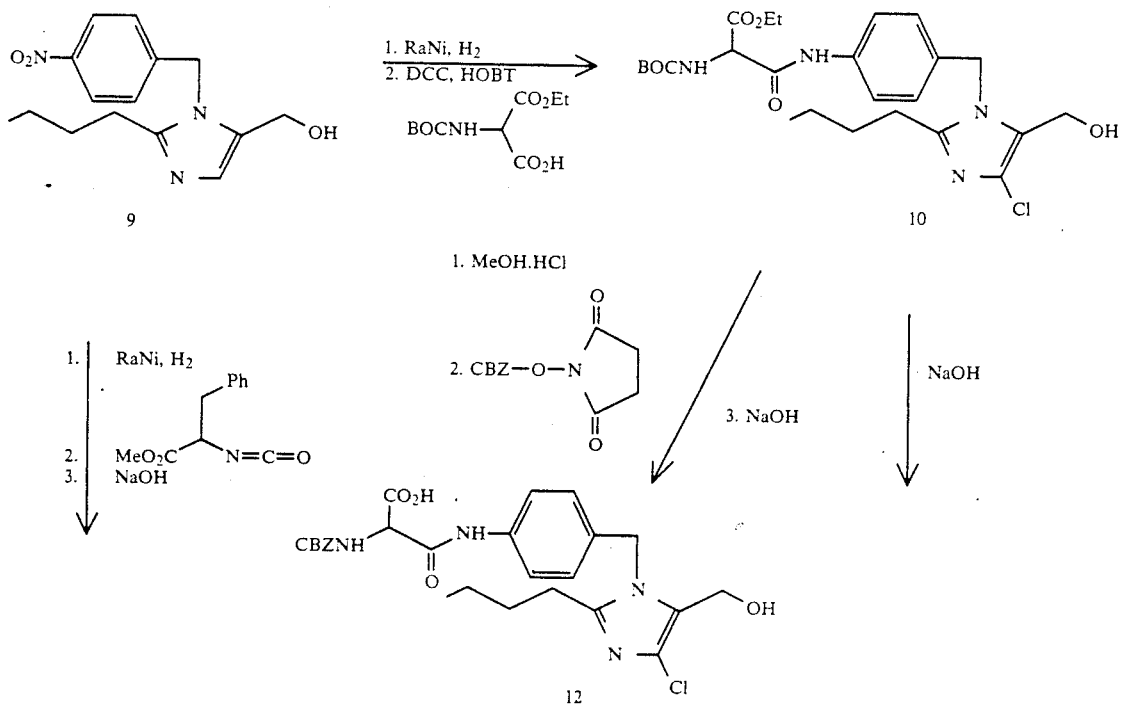

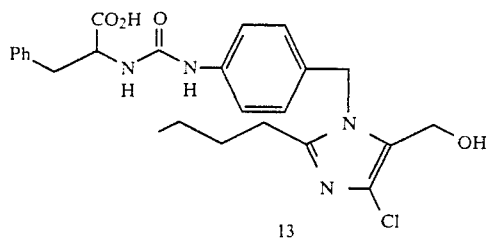
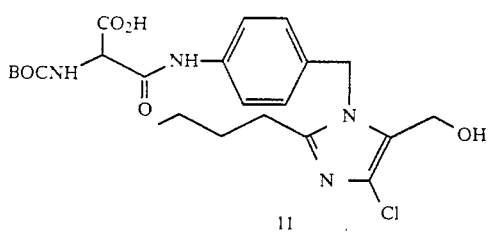

-continued
Scheme II

The effectiveness of the compounds of the instant invention is determined by a test (RBAT) entitled Receptor Binding of Angiotensin II. In this in vitro test the inhibition of tritiated angiotensin II binding to rat liver membranes is measured.

TABLE II

| Example Number | RBAT IC$_{50}$* ($\mu$M) |
| --- | --- |
| 5 | 3.0 |
| 6 (4-Chloro) | 3.0 |
| 6 | 4.5 |
| 9 | >10 |
| 7 | 4.0 |
| 11 | 6.0 |
| 13 | 10.0 |
| 16 | 2.5 |
| 17 | 3.6 |
| 18 | >10 |

*The IC$_{50}$ is a concentration required to displace 50% of the specific bound tritiated angiotensin II.

Based on the observations that ACE inhibitors are known to benefit patients with heart failure, the instant compound which also interrupts the renin angiotensin system (RAS), would show similar benefits.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents. It can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquified form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 0.1 to 1500 mg/kg of body weight per day or preferably 1 to 500 mg/kg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

1-[(4-Aminophenyl)methyl]-2-butyl-4-chloro-1H-imidazole-5-methanol

Part 1

2-Butyl-4-chloro-1-[(4-nitrophenyl)methyl]-1H-imidazole-5-methanol. This compound was prepared in a manner analogous to that of Furakawa, et al, U.S. Pat. No. 4,355,040, Example 17. MP 91°–93° C. MS (EI) 324 (m+1).

Part 2

1-[(4-Aminophenyl]methyl]-2-butyl-4-chloro-1H-imidazole-5-methanol. A solution of the product from Part 1 (3.9 g) in THF (100 mL) was treated with Raney nickel (1.5 g) and hydrogenated at 50 psi for 3.5 hours. Catalyst was removed by filtration and the filtrate was evaporated. The resulting crystalline mass was triturated with isopropyl ether to give the title compound (3.2 g). MP 101°–103° C. MS (EI) 293 (m).

EXAMPLE 2

1-[(4-Aminophenyl)methyl]-5-(ethylthio)-1H-1,3,4-triazole-2-methanol

Part 1

[4-(Nitrophenyl)methyl]-carbamothioic acid, hydroxyacetyl)hydrazide. 4-nitrobenzylamine HCl (3.8 g) was partitioned between CH$_2$Cl$_2$ (75 mL) and 0.5N NaOH (50 mL). The organic layer was dried over MgSO$_4$ and filtered. The filtrate was treated with di-2-pyridylthiocarbonate (*Tetr. Lett.* 26, 1661 (1985), 4.64 g) and stirred at room temperature for 45 minutes. The resulting solution was treated with a solution of glycolic acid hydrazide (1.8 g) in methanol (25 mL) and the reaction was stirred overnight. The resulting suspension was filtered to afford the title hydrazide (5.2 g). MP 202√–204° C. MS (EI) 284 (m).

Part 2

5-Mercapto-4-[[4-nitrophenylmethyl]-4H-1,2,4-triazol-3-methanol. The product from Part 1 (5.0 g) was dissolved in 2 N NaOH (35 mL) and heated on a steam bath until the pot temperature reached 80° C. The resulting solution was then cooled on an ice bath while adding 2 N HCl (36 mL). The resulting yellow solid was collected by filtration and dried to afford the desired triazole (4.5 g). MP 219°–221° C. MS (EI) 266 (m).

Part 3

5-(Ethyltio)-1[(4-nitrophenyl)methyl]-1H-1,3,4-triazole-2-methanol. The product from Part 2 (1.8 g) was dissolved in DMF (15 mL) and treated with diisopropylamine (1.43 mL) and iodoethane (0.66 mL). The reaction was stirred overnight at room temperature then evaporated. The residue was partitioned between EtOAc and water and the organic layer was washed with 0.1 N HCl, dried over MgSO$_4$, and evaporated to an oil. The oil was dissolved in CH$_2$Cl$_2$ and evaporated again to give a solid that was triturated with ether to give the desired triazole (1.6 g). Two batches prepared in the same manner (3.2 g) were recrystallized from EtOAc (150 mL) to give analytically pure material (2.87 g). MP 143°–145° C. MS (EI) 295 (m+1).

1-[(4-Nitrophenyl)methyl]-5-(1-propylthio)-1H-1,3,4-triazole-2-methanol. This compound is prepared in an analogous fashion by substituting 1-iodopropane fo iodoethane.

Part 4

1-[(4-Aminophenyl]methyl]-5-(ethylthio)-1H-1,3,4-triazole-2-methanol. The product from Part 3 (2.35 g) was dissolved in MeOH (100 mL) and treated with Raney nickel (0.5 g). The resulting suspension was hydrogenated at 50 psi for 2.5 hours and then filtered. The filtrate was evaporated to a solid that was triturated with cold MeOH and filtered to give the title product as a yellow solid (1.55 g). MP 145°–147° C. MS (EI) 264 (m).

1-[(4-Aminophenyl)methyl]-5-(1-propylthio)-1H-1,3,4-triazole-2-methanol. This compound is prepared in an analogous fashion from the latter compound described in Part 3.

EXAMPLE 3

2-Butyl-4-chloro-5-(cyanomethyl)-1-[(4-nitrophenyl)-methyl]imidazole

The product from Example 1, Part 1 (2.0 g) was dissolved in CHCl$_3$ (20 mL) and treated with SOCl$_2$ (1 mL). After 1 hour at room temperature the reaction was evaporated and the residue was redissolved in CHCl$_3$ (40 mL), diluted with toluene (25 mL), and evaporated again. The residue was dissolved in CHCl$_3$ (20 mL) and treated with a solution of NaCN (1.7 g), (nBu)$_4$NCl (0.2 g) and water (10 mL). The two-phase mixture was stirred vigorously for 2 hours at room temperature then the organic layer was separated, dried over MgSO$_4$ and evaporated. Flash chromatography on silica gel (CHCl$_3$) gives the title compound (1.85 g). MP 118°–121° C. IR (CHCl$_3$) 2240 cm$^{-1}$ ($\equiv$N).

EXAMPLE 4

Methyl 2-butyl-4-chloro-1[(4-nitrophenyl)methyl]imidazol-5-yl-acetate

A mixture of the product from Example 3 (1.8 g) and 6N HCl (40 mL) was heated at reflux for 2 hours. Twenty percent NaOH was added dropwise until a gummy precipitate appeared. The precipitate was extracted into CHCl₃-MeOH (95:5) and the organic phase was dried over MgSO₄ and evaporated. The resulting solid was dissolved in MeOH (100 mL) and treated with trimethyl orthoformate (5 mL). This solution was saturated with anhydrous HCl and heated at reflux for 6 hours. Evaporation gave a residue that was partitioned between 0.25M potassium phosphate pH 7.0 buffer (200 mL) and EtOAc (125 mL). The organic layer was dried over MgSO₄ and evaporated to give the desired ester. $^1$H-NMR (CDCl₃) δ8.3 (d, 2H), 7.1 (d, 2H), 5.3 (s, 2H), 3.6 (s, 3H), 3.5 (s, 2H), 2.6 (t, 2H), 1.7 (m, 2H), 1.4 (m, 2H), 0.9 (5, 3H).

EXAMPLE 5

(S)-[2-[[4-[[2-Butyl-4-chloro-5-(hydroxymethyl)-1H-imidazol-1-yl]methyl]phenyl]amino]-1-(cyanomethyl)-2-oxoethyl]-carbamic acid, phenylmethyl ester A mixture of CBZ-NIA (prepared according to the method described in *Tetra. Lett.*, 23, 149 (1982), 769 mg), DCC (640 mg), HOBT.H₂O (420 mg) and DMF (6 mL) was stirred for 15 minutes at 10° C. and the resulting slurry was treated with a solution of the product of Example 1 (910 mg) in CH₂Cl₂-DMF (9:1, 10 mL). The reaction mxiture was stirred at room temperature for 48 hours. The slurry was then concentrated to remove CH₂Cl₂ and the concentrate was diluted with EtOAc and filtered. Evaporation of the filtrate gives a gum which was partitioned between EtOAc and H₂O. The organic layer was dried over MgSO₄ and evaporated to a foam. Flash chromatography on silica gel (CHCl₃-MeOH, 98:2) gives the desired product (1.2 g) as a solid upon trituration with ether. MP 89°–91° C. MS (FAB) 524 (m+1).

EXAMPLE 6

(S)-[2-[[4-[[2-Butyl-4-chloro-5-(hydroxymethyl)-1H-imidazol-1-yl]methyl]phenyl]amino]-1-[(4-hydroxyphenyl)methyl]-2-oxoethyl]-carbamic acid, 1,1-dimethylethyl ester and
(S)-[2-[[4-[[2-butyl-5-(hydroxymethyl)-1H-imidazol-1-yl]methyl]phenyl]amino]-1-[(4-hydroxyphenyl)methyl]-2-oxoethyl]-carbamic acid, 1,1-dimethylethyl ester A mixture of BOC-(OBn)TYR (1.3 g), DCC (0.73 g, HOBT.H₂O(0.48 g), and DMF (7 mL) was stirred for 30 minutes at 10° C. and the resulting suspension was treated with a solution of the product of Example 1 (1.04 g) in CH₂Cl₂-DMF (5:3, 8 mL). The reaction mixture was stirred at room temperature for 48 hours and worked up as in Example 5. Trituration of the residue from the EtOAc layer with ether gave a solid that was collected by filtration to give the major product (1.9 g) as pure material without chromatography. TLC (silica gel, CHCl₃-MeOH, 9:1, $R_f$=0.4. A portion of this material (875 mg) was dissolved in MeOH (10 mL), treated with 20% Pd/C (50 mg) and hydrogenated at 1 atm for 2 hours. Catalyst was removed by filtration and the filtrate was evaporated. Flash chromatography on silica gel (CHCl₃-MeOH, 97:3 to 88:12 gradient) gave two products. The faster eluting material is the chlorinated product (300 mg). MS (FAB) 557 (m+1). The slower eluting material is the des-chloro product (400 mg). MS (FAB) 523 (m+1).

EXAMPLE 7

(S)-4-[[4-[[2-Butyl-4-chloro-5-(hydroxymethyl)-1H-imidazol-1-yl]methyl]phenyl]amino]-4-oxo-3-[[(phenylmethoxy)carbonyl]amino]-butanoic acid, 1,1-dimethyethyl ester CBZ-(OtBu)ASP.dicyclohexylamine (1.32 g) was partitioned between CH₂Cl₂ (35 mL) and 0.1N HCl (35 mL). The organic layer was dried over MgSO₄ and evaporated. The residue was dissolved in DMF (10 mL) and added to a 10° C. solution of DCC (0.52 g) and HOBT.H₂O (0.34 g) in DMF (10 mL). The resulting mixture was stirred 15 minutes at room temperature and treated with a solution of the product from Example 1 (0.73 g). The reaction was stirred 48 hours at room temperature and worked-up as in Example 5. The residue from the EtOAc layer was dissolved in CHCl₃ and evaporated to give a solid that was triturated with ether. The resulting solid was recrystallized from CHCl₃-ether to give the title compound (0.89 g). MP 153°–155° C. MS (FAB) 599 (m+1).

EXAMPLE 8

(S)-4-[[4-[[2-Butyl-4-chloro-5-(hydroxymethyl)-1H-imidazol-1-yl]methyl]phenyl]amino]-4-oxo-3-[[(phenylmethoxy)carbonyl]amino]-butanoic acid A solution of the product from Example 7 (0.7 g) in CH₂Cl₂ (10 mL) was treated with trifluoroacetic acid (20 mL) and the resulting mixture was stirred 5 hours at room temperature. 1,2-Dichloroethane (50 mL) was added and the solvents were evaporated. The residue was dried to constant weight under a vacuum (0.5 mm Hg) then purified by flash chromatography on silica gel (CHCl₃-MeOH, 99:1 to 94:6 gradient). Trituration with ether gave the title compound as an off-white powder (0.48 g). MS (FAB) 543 (m+1).

EXAMPLE 9

(S)-4-[[4-[[3-(Ethylthio)-5-(hydroxymethyl)-4H-1,2,4-triazol-4-yl]methyl]phenyl]amino]-4-oxo-3-[[phenylmethoxy)carbonyl]amino]-butanoic acid Methods from Examples 7 and 8 were employed to prepare the title compound, using the product from Example 2 in place of the product from Example 1 as starting material. MS (FAB) 1027 (2m+1), 514 (m+1).

EXAMPLE 10

(RS)-3-[[4-[2-Butyl-4-chloro-5-(hydroxymethyl)-1H-imidazol-1-yl]methyl]phenyl]amino]-2-[[(1,1-dimethylethoxy)carbonyl]amino]-3-oxo-propanoic acid, ethyl ester Using the method described in Example 5, the product of Example 1 was coupled to BOC-(EtO)AMA (prepared according to procedures described in *Organic Syntheses*, Col. Vol. V, p. 373, and in the *J. Am. Chem. Soc.*, 75, 1970 (1953)). The product was purified by flash chromatography on silica gel (CHCl₃-iPrOH, 92:2 to 96:4 gradient). $^1$N-NMR (CDCl₃) δ 8.6 (br, 1H), 7.5 (d, 2H), 7.0 (d, 2H), 5.9 (d, 1H), 5.2 (s, 2H), 5.0 (d, 1H), 7.5 (d, 2H), 1.3 (m, 2H), 2.6 (t, 2H), 1.7 (m, 2H), 1.5 (s, 9H), 1.3 (m, 5H), 0.9 (t, 3H).

EXAMPLE 11

(RS)-3-[4-[2-Butyl-4-chloro-5-(hydroxymethyl)-1H-imidazol-1-yl]methyl]phenyl]amino]-2-[[(1,1-dimethylethoxy)carbonyl]amino]-3-oxo-propanoic acid The product from Example 10 (0.35 g) was dissolved in MeOH (2 mL), diluted with THF (4 mL), and treated at room temperature with 1 N NaOH (0.7 mL). After 1 hour, 1 N HCl (0.7 mL) was added and the reaction mixture was partitioned between water and EtOAc. The organic layer was dried over MgSO₄ and evaporated. The resulting residue was triturated with ether to give the title compound (0.27 g).

MP 144°–147° C. (gas evol.). MS (FAB) 495 (m+1).

EXAMPLE 12

(RS)-3-[[4-[[2-Butyl-4-chloro-5-(hydroxymethyl)-1H-imidazol-1-yl]methyl]phenyl]amino]-3-oxo-2-[[(phenylmethoxy)-carbonyl]amino]-propanoic acid, ethyl ester The product from Example 10 (0.55 g) was dissolved in CH₂Cl₂ (10 mL) and treated with freshly prepared methanolic HCl (10 mL). After 3 hours at room temperature the solution was evaporated, the residue was dissolved in MeOH (1 mL) and this solution was added dropwise to vigorously stirred ether (100 mL). The resulting precipitate (0.6 g) was collected by filtration. This solid was dissolved in MeOH (5 mL), chilled on an ice bath and treated with a solution composed of N-(benzyloxycarbonyloxy)succinimide (0.25 g), triethylamine (0.28 mL) and CH₂Cl₂ (5 mL). The reaction was stirred for 24 hours at room temperature and the resulting solution was evaporated. The residue was partitioned between EtOAc and water and the organic layer was washed consecutively with 5% NaHCO₃ and saturated with NaCl, dried over MgSO₄ and evaporated. Flash chromatography on silica gel (CHCl₃-MeOH, 98:2) was employed to purify the major product which was evaporated from EtOAc solution to give the title compound (0.39 g) as a solid. $^1$H-NMR (CDCl₃) δ 8.6 (br, 1H), 7.4 (d, 2H), 7.3 (s, 5H), 6.8 (d, 2H), 6.1 (d, 1H), 5.1 (s, 2H), 5.0 (d, 1H), 4.5 (s, 1H), 4.2 (q, 2H), 2.5 (t, 2H), 1.6 (m, 2H), 1.3 (m, 2H), 1.2 (t, 2H), 0.8 (t, 3H).

EXAMPLE 13

(RS)-3-[[4-[[2-Butyl-4-chloro-5-(hydroxymethyl)-1H-imidazol-1-yl-methyl]phenyl]amino]-3-oxo-2[(phenylmethoxy)-carbonyl]amino]-propanoic acid The product from Example 12 was saponified using the procedure from Example 10 to afford the title compound. MS (FAB) 551 (m+Na), 529 (m+1).

EXAMPLE 14

(RS)-2-(Acetylamino)-3-[4-[[2-butyl-4-chloro-5-(hydroxymethyl)-1H-imidazol-1-ylmethyl]phenyl]amino]-3-oxo-propanoic acid, 1,1-dimethylethyl ester Part 1

Acetamidomalonate mono-t-butyl ester. Methyl, t-butyl malonate (Fluka Chemical Co.) was converted to methyl, t-butyl aminomalonate using procedures described in *Organic Syntheses*, Col. Vol. V, p. 373, and in the *J. Am. Chem. Soc.*, 75, 1970 (1953). Acetylation using acetic anhydride and triethylamine in CH₂Cl₂ gave acetamidomalonate methyl, t-butyl ester. Saponification of the methyl ester as in Example 10 gave Ac-(t-BuO)AMA. $^1$H-NMR (CDCl₃) δ 8.9 (br, 1H), 7.8 (d, 1H), 5.0 (d, IH), 2.1 (s, 3H), 1.5 (s, 9H).

Part 2

(RS)-2-(Acetylamino)-3-[[4-[[2-butyl-4-chloro-5-(hydroxymethyl)-1H-imidazol-1-yl]methyl]phenyl]amino]-3-oxo-propanoic acid, 1,1-dimethylethyl ester. The product from Part 1 was coupled to the product from Example 1 using the method described in Example 5 to give the title compound. $^1$H-NMR (CDCl₃) δ 8.7 (s, IH), 7.5 (d, 2H), 7.0 (d, 2H), 6.8 (d, 1H), 5.2 (s, 2H), 5.1 (d, 1H), 4.5 (d, 2H), 2.6 (t, 2H), 2.1 (s, 3H), 1.7 (m, 2H), 1.6 (s, 9H), 1.4 (m, 2H), 0.9 (t, 3H).

EXAMPLE 15

(RS)-2-(Acetylamino)-3-[[4-[[2-butyl-4-chloro-5-(hydroxymethyl)-1H-imidazol-1-yl]methyl]phenylamino]-3-oxo-propanoic acid The t-butyl ester in the product from Example 14 was cleaved using the method described in Example 8. The crude product was purified by flash chromatography on silica gel (CHCl³ to CHCl³-MeOH, 95:5 gradient). The resulting gum was triturated with ether to give a solid. MS (FAB) 437 (m+1).

EXAMPLE 16

(S)-N-[4-[[2-Butyl-4-chloro-5-(hydroxymethyl)-1H-imidazol-1-yl-methyl]phenyl-2-[(4-morpholinyl-sulfonyl)amino]-3-phenylpropanamide Part 1

N-(4-MorpholinYlsulfonyl)-L-phenylalanine. A solution of L-PHE (66 g), NaOH (16 g), and water (120 mL) was treated dropwise with a solution of 4-morpholinylsulfamyl chloride (37 g, prepared according to the methods of R. Wegler and K. Bodenbenner, *Anallen der Chemie*, 624, 25 (1959) and G. Weiss and G. Schulze, *Anallen der Chemie*, 729, 40 (1969)) in THF (80 mL). The reaction was stirred for 6 hours at room temperature then concentrated aqueous HCl was added dropwise to bring the solution to pH 2. Product was extracted into EtOAc and this solution was washed with lN HCl, dried over MgSO₄ and evaporated. The residue was triturated with ether to give a solid that was recrystallized from water to give morpholinylsulfonyl-PHE. MP 157°–158° C. MS (FAB) 337 (m+Na), 315 (m+1).

Part 2

Using the method described in Example 5, the product of Example 1 was coupled to morpholinyl-sulfonyl-PHE to give the title compound which was purified by flash chromatography on silica gel (CH₂Cl₂-MeOH, 9:1). MS (FAB) 590 (m+1).

EXAMPLE 17

(S)-2-(Benzenesulfonylamino)-N-[4-[[2-butyl-4-chloro-5-(hydroxymethyl)-1H-imidazol-1-yl]methvlphenyl-3-phenylpropanamide Using the method described in Example 5 and 16, the product of Example 1 was coupled to benzene-sulfonyl-PHE to give the title compound which was purified by flash chromatography on silica gel (CH₂Cl₂-MeOH, 9:1). MS (FAB) 581 (m+1).

EXAMPLE 18

1-[[4-[[2-Butyl-4-chloro-5-(hydroxymethyl)-1H-imidazol-1-yl]methyl]phenyl]amino]carbonyl-2-pyrrolidinecarboxylic acid, methyl ester Part 1

N-Chlorocarbonyl-L-proline methyl ester. A suspension of L-proline methyl ester.HCl (5 g) in CHCl₃ (100 mL) was treated with a stream of anhydrous ammonia for 15 minutes. NH₄Cl was removed by filtration and the filtrate was evaporated. The residue was redissolved in CHCl₃ (50 mL) and treated with excess phosgene (an 18% (w/w) solution in CHCl₃, 48 g of solution). The reaction mixture was stirred at room temperature, overnight, under N₂ atmosphere. Evaporation gave the desired carbamyl chloride.

Part 2

A solution of the product from Part 1 (0.47 g), CH$_2$Cl$_2$ (15 mL), DMF (6 mL) and Et$_3$N (0.27 mL) was treated with a solution of the product from Example 1 (0.39 g) in CH$_2$Cl$_2$ (3 mL). The reaction was stirred at room temperature for 20 hours and solvents were evaporated. The residue was partitioned between H$_2$O and CH$_2$Cl$_2$ and the organic layer was dried over MgSO$_4$ and evaporated. Flash chromatography on silica gel (CHCl$_3$-MeOH, 99:1) gives the desired product. MS (CI) 449 (m+1)

I claim:

1. A compound of formula

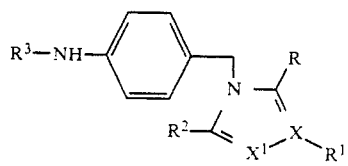

a pharmaceutically acceptable acid addition or base salt thereof, wherein:

X and X$^1$ are nitrogen;
R and R$^1$ are each independently
  hydrogen,
  halogen,
  lower alkyl,
  alkyl carboxylate,
  trihalomethyl,
  acetyl ester,
  cyano,
  cyanomethyl,
  acetamide,
  alkoxymethyl,
  hydroxymethyl,
  alkylthiomethyl,
  thiomethyl,
  COOH,
  CHO,
  1-oxoalkyl,
  2-oxoalkyl, or
  3-oxoalkyl
with the proviso that when X is nitrogen, R$^1$ is absent, R$^2$ is propyl,
  butyl,
  —CH$_2$CH=CH$_2$,
  —CH=CHCH$_3$,
  —CH$_2$CH=CH—CH$_3$,
  —CH=CHCH$_2$Ch$_3$,
  —CH$_2$CH$_2$CH=CH$_2$
  —CH$_2$C≡CH,
  —C≡C—CH$_3$,
  —C≡C—CH$_d$,
  —CH$_2$C≡CCH$_3$,
  —CH$_2$CH$_2$C≡CH,
  —SCH$_3$,
  —SC$_2$H$_5$,
  —SC$_3$H$_7$,
  —SC$_4$H$_9$,
  —OCH$_3$,
  —OC$_2$H$_5$,
  —OC$_3$H$_7$,
  —OC$_4$H$_9$,
  —SCH$_2$CH=CH$_2$, or
  —OCH$_2$CH=CH$_2$;
  —OCH$_2$C≡CH;
and
R$_3$ is

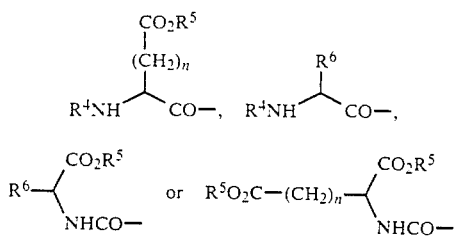

wherein
R$_4$ is
  CBZ,
  BOC,
  -COPh,
  —COCH$_2$CH$_3$,
  —COCH$_3$,
  —COCF$_3$,
  —CONH$_2$,
  —CONHCH$_3$,
  —CON(CH$_3$)$_2$,
  —SO$_2$CH$_3$,
  —SO$_2$CF$_3$,

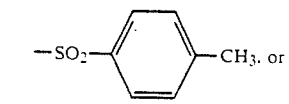, or

—SO$_2$Ph;
R$_5$ is
  H,
  CH$_3$,
  C$_2$H$_5$,
  t—C$_4$H$_9$,
  CH$_2$Ph;
n is 0-3; and
R$_6$ is
  H
  CH$_3$,
  C$_2$H$_5$,
  C$_3$H$_7$
  i—C$_3$H$_7$,
  C$_4$H$_9$,
  i—C$_4$H$_9$,
  CH$_2$CH(CH$_3$)CH$_2$CH$_3$,
  CH$_2$CH=CH$_2$,
  CH$_2$-cyclohexyl,
  CH$_2$—Ph,

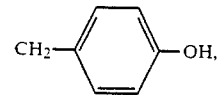

CH$_2$CN,
  (CH$_2$)$_4$NH$_2$,
  (CH$_2$)$_3$NH$_2$,

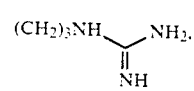

CH₂OH,
CH(CH₃)OH,
CH₂SH,
CH₂CH₂SCH₃,
CH₂CONH₂, or
CH₂CH₂CONH₂.

2. A compound according to claim 1 wherein
X and X¹ are each independently carbon or nitrogen;
R and R¹ are each independently,
—CH₂OH,
—CH₂SH
—CH₂OCH₃,
—CH₂SCH₃,
—CHO
—CO₂CH₃
—C≡N

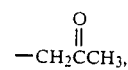

—CO₂C₂H₅;
—COOH,
—CF₃,
—CH₃,
—H,
—Cl,
—Br,
—F,
—CH₂CO₂CH₃,
—CH₂CO₂C₂H₅,
—CH₂≡N,
—CH₂CONH₂,
—CH₂CONHCH₃, or
—CH₂CON(CH₃)₂
with the proviso that when X is nitrogen, R¹ is absent;
R²
is propyl,
butyl,
thiomethyl,
thioethyl,
thiopropyl,
thiobutyl,
—CH₂CH=CH₂,
—CH₂CH=CH—CH₃,
—CH₂CH₂CH=CH₂,
—CH₂C≡CCH₃,
—CH₂CH₂C≡CH,
—OCH₃,
—OCH₂H₅,
—OC₃H₇,
—OC₄H₉,
—SCH₂CH=CH₂ or
—OCH₂CH=CH₂; and
R₃ is as above.

3. A compound according to claim 1 wherein
X is carbon or nitrogen;

X¹ is nitrogen;
R and R¹ are each independently,
—H,
—CH₂OH,
—CH₂OCH₃,
—CH₂CO₂CH₃,
—Cl
—Br, or
—CF₃
with the proviso that when X is nitrogen R¹ is absent;
R₂ is
—C₄H₉,
—C₃H₇,
—SC₂H₅, or
—SC₃H₇; and
R₃ is

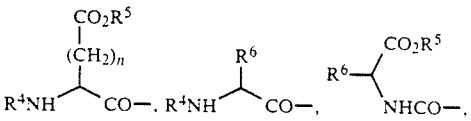

wherein
R⁴ is
CBZ,
BOC,
COPh,
COCH₃,
SO₂Ph;
n is 0-2;
R⁵ is
—H,
—CH₃,
—CH₂H₅,
—t—C₄H₉ or
—CH₂Ph; and
R⁶ is
—CH₃,
—iC₃H₇,
—iC₄H₉,
—CH₂CH(CH₃)CH₂CH₃,
—CH₂pH,

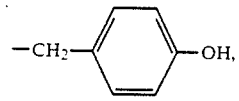

—CH₂OH,
—CH₂SH, or
—CH(CH₃)OH.

4. A compound selected from the list consisting of:
(S)-4-[[4-[[3-Ethylthio)-5-(hydroxymethyl)-4H-1,2,4-triazole-4-yl]methyl]phenyl]amino]-4-oxo-3-[[phenylmethoxy)carbonyl]amino]butanoic acid.

* * * * *

UNITED STATES PATENT AND TRADEMARK OFFICE
CERTIFICATE OF CORRECTION

PATENT NO. : 5,041,552

DATED : August 20, 1991

INVENTOR(S) : John C. Hodges, et al.

It is certified that error appears in the above-identified patent and that said Letters Patent is hereby corrected as shown below:

Column 23, delete lines 49, 51, and 53-55.

Column 24, delete line 1.

Column 24, add "$CH_2\text{-}C_6H_4\text{-}OCH_3$," after structure on lines 55-60.

Column 26, line 44, should read "$CH_2Ph$,".

Column 26, line 54, delete "selected from the list consisting of" and insert instead "named".

Signed and Sealed this

Twenty-third Day of March, 1993

Attest:

STEPHEN G. KUNIN

Attesting Officer     Acting Commissioner of Patents and Trademarks